United States Patent [19]

Takeuchi et al.

[11] Patent Number: 4,882,314

[45] Date of Patent: Nov. 21, 1989

[54] A COMPOSITION AND METHOD OF TREATING SELECTED MALIGNANT CONDITIONS

[75] Inventors: Setsuo Takeuchi, Higashiyamato; Mutsuyuki Kochi, No. 19 Matsudashinden, Matsudo-shi, Chiba-ken; Akira Kawarada, Tokyo; Shinichiro Esumi, Kunitachi; Kaguya Sasaki, Higashikurume; Shozo Kawabata, Kawagoe; Tsuneo Saita; Yukio Inoue, both of Tokyo; Makoto Yamamoto, Tokyo; Keiji Sekine, Yono, all of Japan

[73] Assignees: Rikagaku Kenkyusho, Wako; Mutsuyuki Kochi, Matsudshi; Kaken Kagaku Kabushiki Kaisha, Tokyo, all of Japan

[21] Appl. No.: 81,480

[22] Filed: Aug. 4, 1987

Related U.S. Application Data

[63] Continuation of Ser. No. 803,412, Dec. 2, 1985, abandoned, which is a continuation of Ser. No. 567,961, Jan. 4, 1984, abandoned, which is a continuation of Ser. No. 424,401, Sep. 27, 1982, abandoned, which is a continuation of Ser. No. 275,369, Jun. 19, 1981, abandoned, which is a continuation of Ser. No. 155,401, Jun. 2, 1980, abandoned.

[51] Int. Cl.$^4$ .............................................. A61K 31/70
[52] U.S. Cl. ....................................................... 514/23
[58] Field of Search .......................................... 514/23

Primary Examiner—Jerome D. Goldberg
Attorney, Agent, or Firm—Bucknam and Archer

[57] ABSTRACT

Disclosed is a novel carcinostatic composition comprising 4,6-0-benzylidene-D-glucopyranose as the active ingredient. This active ingredient exerts a very high carcinostatic activity according to a specific carcinostatic mechanism quite different from that of conventional carcinostatic chemotherapeutic agents. The active ingredient is very low in toxicity and is highly stable and water-soluble. This composition is effective against selected malignant conditions which are carcinoma of the colon, cancer of the stomach, cancer of the tongue, peritonitis carcinomatosa, cancer of the liver and malignancies induced by SV$_{40}$ virus.

7 Claims, 2 Drawing Sheets

A COMPOSITION AND METHOD OF TREATING SELECTED MALIGNANT CONDITIONS

This application is a continuation of Ser. No. 803,412 filed Dec. 2, 1985, which is a continuation of U.S. Pat. No. 567,961 filed Jan. 4, 1984; which is a continuation of U.S. Pat. No. 424,401 filed Sept. 27, 1982; which is a continuation of U.S. Pat. No. 275,369 filed June 19, 1981; which is a continuation of U.S. Pat. No. 155,401 filed June 2, 1980, all of which have now been abandoned. Also, Ser. No. 744,867, filed Mar. 7, 1977; Ser. No. 942,402 filed Sept. 14, 1978 and Ser. No. 84,540 filed Oct. 15, 1979 have been abandoned.

FIELD OF THE INVENTION

The present invention relates to a novel composition comprising 4,6-O-benzylidene-D-glucopyranose as the active ingredient. The term "carcinostatic" as used herein refers to a composition effective against selected malignant conditions which are carcinoma of the colon, cancer of the stomach, cancer of the tongue, peritonitis carcinomatosa, cancer of the liver and malignancies induced by $SV_{40}$ virus.

As agents in cancer chemotherapy, there have heretofore been used alkylating agents such as nitrogen mustards, ethylene imines and sulfonic acid esters, antimetabolites such as folic acid antagonists, purine antagonists and pyrimidine antagonists, vegetable mitotic poisons such as Colcemid and Vinblastine, antibiotic substances such as sarkomycin, carzinophilin and mitomycin, hormones such as adrenal steroid, male hormone and female hormone, and porphyrine complexes such as Merphyrin and COPP. The nucleic acid inhibiting action of carcinostatic agents ordinarily affects not only cancer cells but also normal cells, and these carcinostatic agents have a high toxicity and produce serious side effects. Accordingly, it is very difficult to attain sufficient effects by high dosages of carcinostatic agents as in case of chemotherapeutic agents for treating infectious diseases.

We previously developed a novel and valuable composition comprising benzaldehyde as the active ingredient (Japanese Patent Publication No. 962/79 corresponding to U.S. Ser. No. 84,540 filed on Oct. 15, 1979 as a continuation application of U.S. Ser. No. 942,402, which was filed on Sept. 14, 1978 as a continuation application of U.S. Ser. No. 774,867, filed on Mar. 7, 1977). It was found that this active ingredient does not directly attack cancer cells, but that it is a specific agent which produces a therapeutic effect according to a mechanism quite different from the therapeutic mechanism heretofore considered for conventional chemotherapeutic agents. We furthered our research and investigations with a view to finding effective substances, and as a result, we have found that a specific aromatic aldehyde derivative has a activity, and that it exerts prominent effects in the treatment of cancers. Based on this finding, we have now completed the present invention of a composition.

Most conventional carcinostatic chemotherapeutic agents are substances toxic to living cells, which are more effective against transplanted tumors such as Ehrlich carcinoma than against malignant cells induced by oncogenic virus $SV_{40}$. On the other hand, the active ingredient of the present invention is highly effective against malignant cells induced by oncogenic virus $SV_{40}$ and it is considered that the active ingredient of the carcinostatic composition of the present invention has a carcinostatic mechanism quite different from that of the conventional carcinostatic chemotherapeutic agents. In short, the active ingredient of the composition of the present invention has excellent specific carcinostatic characteristics.

For example, the active ingredient of the present invention which has a prominent effect is very stable, lowly toxic, water-soluble and has a broad effective concentration range. From the results of clinical experiments, it was found that when the active ingredient of the present invention is administered intravenously at a dosage of about 20 to about 200 mg/day/man, there is attained a prominent effect on colon carcinoma, tongue cancer, peritonitis carcinomatosa, liver cancer and stomach cancer.

The composition of the present invention have very high stability and is very effective against various cancerous diseases. It is considered that the active ingredient of the present invention is excellent as a chemotherapeutic agent when administered to humans, domestic animals, dogs, cats and other warm-blooded animals.

SUMMARY OF THE INVENTION

It is therefore a primary object of the present invention to provide a carcinostatic composition comprising 4,6-O-benzylidene-D-glucopyranose as the active ingredient.

Another object of the present invention is to provide a pharmaceutical preparation, which is suitable for administration, of 4,6-O-benzylidene-p-glucopyranose as a agent.

Still another object of the present invention is to provide a method for treating malignant conditions in which a composition comprising 4,6-O-benzylidene-D-gluccopyranose as the active ingredient is administered.

Other objects of the present invention will become apparent from the following detailed description.

BRIEF DESCRIPTION OF THE DRAWINGS

FIG. 1-B shows the C.T. scan taken in the same region from the same direction in FIG. 1-A, in the patient of FIG. 1-A, after the treatment with the composition of the present invention.

FIG. 2-B is a photograph taken in the same region from the same direction as in FIG. 2-A, in the patient of FIG. 2-A after the treatment with the carcinostatic composition of the present invention.

FIG. 3-A is a color photograph of FIG. 2-A and FIG. 3-B is a color photograph of FIG. 2-B.

DETAILED DESCRIPTION OF THE PREFERRED EMBODIMENTS

Figure 1A:
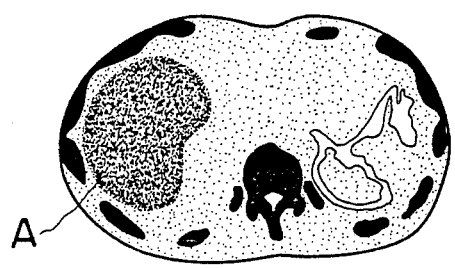
FIG. 1-A shows the C.T. scan (X-ray tomogram) of metastatic cancer in the liver of a patient suffering from colon carcinoma before the treatment with the carcinostatic composition of the present invention.

The carcinostatic composition of the present invention comprises as the active ingredient 4,6-benzylidene-D-glucopyranose having activity. This compound is represented by the following structural formula:

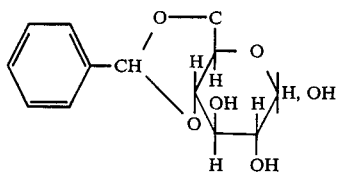

and has a melting point of 196°~187° C. [see H. G. Fletcher, Jr., Methods in Carbohydrate Chemistry, vol. 2,307 (1963)].

As described hereinafter, the carcinostatic composition of the present invention can be applied by either oral administration or non-oral administration. In case of oral administration, the composition of the present invention may be applied in the form of a soft capsule, a hard capsule, a tablet, granules such as coarse granules or fine granules, or powders. In case of non-oral administration, it may be administered in the form of an injection (intravenous, subcutaneous intraperitoneal injection), an intravenous drip, or a solid or suspension viscous preparation that can be absorbed continuously from a mucosa, such as a suppository.

In forming a pharmaceutical preparation containing the active ingredient of the present invention, 4,6-O-benzylidene-D-glucopyranose, the active ingredient may be formed into an aqueous solution or emulsion or suspension or an oil base according to a customary method, to obtain a liquid preparation for intravenous, subcutaneous or intraperitoneal injection, or it may be molded into a preparation for oral administration, such as a capsule, a microcapsule, a tablet or granules or the like.

As the surface active agent, excipient, lubricant, adjuvant and pharmaceutically acceptable film forming agent that can be used for preparing preparations of the active ingredient of the present invention, there can, for example, be mentioned the following:

As the surface active agent to be used for assisting disintegration or dissolution of the composition of the present invention, there can be mentioned, for example, alcohols, esters, polyethylene glycol derivatives, sorbitan fatty acid esters and sulfated aliphatic alcohols. These surface active agents may be used singly or in the form of a mixture of two or more of them.

As the excipient, there can be mentioned, for example, sucrose, lactose, startch, crystalline cellulose, mannitol, light silicic anhydride, magnesium aluminate, magnesium metasilicate aluminate, synthetic aluminum silicate, calcium carbonate, sodium hydrogencarbonate, calcium hydrogenphosphate and calcium carboxymethyl cellulose. These excipients may be used singly or in the form of a mixture of two or more of them.

At least one member selected from, for example, magnesium stearate, talc and hardened oils may be used as the lubricant. As the taste or smell improving agent (corrigent), there can be used sweetening agents, perfumes, coloring agents and preservatives such as sodium chloride, saccharin, sugar, mannitol, orange oil, licorice extract, citric acid, fructose, glucose, menthol, eucalyptus oil, malic acid and the like.

As the adjuvant, e.g., suspending agent or wetting agent, there can be used, for example coconut oil, olive oil, sesame oil, peanut oil, calcium lactate, safflower oil and soy bean phospholipid.

As the film forming substrate, there can be mentioned, for example, carbohydrate derivatives of celluloses and saccharides, such as cellulose acetate phthalate (CAP), and acrylic acid type copolymers and polyvinyl derivatives of dibasic acid monoesters, such as methyl acrylate/methacrylic acid copolymers and methyl methacrylate/methacrylic acid copolymers.

When the carcinostatic agent is coated with a film forming substance as mentioned above, coating assistants such as plasticizers and several additives for preventing adhesion between the agents during the coating step may be used, thereby the properties of the film forming substance can be improved or the coating operation facilitated.

The dosage is varied to some extent depending on the kind of animal serving as the subject, the condition of the disease, the method of administration, the preparation form, the frequency of administration, the desired effect and the treatment period. In case of injection, the dosage for adults is ordinarily about 0.5 to about 5,000 mg per day, preferably about 5 to about 1,000 mg per day, and more preferably about 10 to about 600 mg per day, as the active compound. The dosage for children is ordinarily about 0.5 to about 3,000 mg per day, preferably about 3 to about 500 mg per day, more preferably about 3 to about 300 mg per day, as the active compound. In case of oral administration, the dosage is ordinarily about 3 times the dosage in case of injection.

The test for confirmation of the carcinostatic activity of 4,6-O-benzylidene-D-glucopyranose and the toxicity of this compound will now be described.

A. Carcinostatic Activity Test:

The $SV_{40}$ (Simian Virus 40) method was adopted for determination of the carinostatic activity. According to this method, normal kidney cells of mice are transformed to malignant cells by the oncogenic virus $SV_{40}$, the malignant cells are cultured, the test compound is added to the culture medium, the ratio of inhibition of proliferation of the cells is calculated and the carcinostatic activity is determined based on the calculated value. This method has recently been widely used because accurate results can be obtained [see proceedings of the Society for Experimental Biology and Medicine, 114, pages 721–727 (1963)].

The W2K.11 cells obtained by a malignant transformation of normal kidney cells of C3H mice by the oncogenic virus $SV_{40}$ were used as cells for the test, and they were cultured according to the following method.

(1) Preparation of Culture Medium:

9.4 g of Eagle MEM Medium (manufactured by Nissui Seiyaku K.K.) was dissolved in 900 ml of distilled water and the solution was sterilized at 120° C., under pressure for 15 minutes. After cooling the sterilized solution, 100 ml of calf serum and 3 to 5 ml of a 10% aqueous solution of sodium hydrogencarbonate sterilized separately at 115° C. under pressure for 15 minutes were added to the solution to adjust the pH to 7.1 to 7.2. Just before the resulting culture medium was used, 10 ml of a L-glutamine solution (2.92 g/100 ml) filtered through A millipore filter was added thereto.

(2) Preparation of Test Cells:

The frozen test cells preserved in a deep freezer (−80° C.) with dimethyl sulfoxide added to the above culture medium to a final concentration of 10% were fused at room temperature and subjected to centrifugal separation under 670×g for 5 minutes. The supernatant was discarded and the precipitated cells were suspended in 50 ml of the culture medium. Then, the culture medium was transferred to a Roux flask and culturing was conducted at 37° C. The cells began to grow while adhering to the bottom of the flask, and sufficient growth was obtained in 3 to 4 days. The culture liquid was decanted and 10 ml of a 0.2% trypsin solution (which was formed by dissolving 4.7 g of Eagle MEM culture medium, 0.6 g of sodium bicarbonate and 1 g of trypsin in 500 ml of distilled water and passing the solution through a millipore filter) was added to the residue to effect the trypsin treatment at room temperature for 2 to 3 minutes. The trypsin solution was removed by decantation. Then, 50 ml of a fresh culture medium was added to the residue, and the cells adhering to the flask were washed out by a Komagome type pipette to obtain a cell suspension. The number of cells in the cell suspensions was adjusted to $0.5 \sim 1.0 \times 10^5$ cells/ml in Eagle MEM culture medium.

(3) Culturing of Cells and Addition of Test Compound:

An aliquot of 1.8 ml of the cell suspension was transferred to a disposal Petri dish (having a diameter of 35 mm) and culturing was conducted at 37° C. in a carbon dioxide gas incubator (5% of $CO_2$ and 95% of air) for 24 hours.

At this point, 0.2 ml of a solution of the test compound was added to the culture liquid and culturing was further continued.

The state of proliferation of the cells was examined every day using an inverted microscope. The number of living cells was counted 48 hours after addition of the test compound.

The test compound was added in the form of a solution formed by dissolving the test compound in distilled water or ethanol (at a final concentration of 2%) and passing the solution through a millipore filter.

(4) Method of Counting the Number of Cells:

When 48 hours had passed from the point of the addition of the test compound, the supernatant (the culture liquid) in the Petri dish was decanted and discarded, and the cells adhering to the bottom of the Petri dish were treated with 1.0 ml of the above-mentioned 0.2% trypsin solution to obtain single cells. After the trypsin solution was removed by decantation, the cells were suspended in a physiological saline solution containing 10 millimols of a phosphate buffer solution (pH=7.0) and 0.1% trypan blue was added to the residue to count the number of viable cells. One or two drops of the cell suspension were collected in a blood cell counter, a cover glass was placed on the counter and the number of cells was counted using a microscope.

The cell proliferation inhibition ratio of the ftest compound was calculated according to the following equation:

$$\text{Inhibition ratio (\%)} = \frac{A - B}{A} \times 100$$

wherein A stands for the number of cells in the Petri dish to which the test compound was not added and B stands for the number of cells in the Petri dish to which the test compound was added.

B. Toxicity:

Since 4,6-benzylidene-D-glucopyranose is a compound having a low molecular weight and thus is readily excreted from a living body when administered, no side effects are caused. Thus, no toxicity is observed when the compound is continuously administered at the above-mentioned dosage.

The acute toxicity of this compound observed on subcutaneous injection or oral administration in mice is much lower than that of other carinostatic agents. The $LD_{50}$ (mg/kg) value of the compound which is the active ingredient of the present invention, for example, in case of oral administration in mice is about 3000 mg/kg.

The present invention will now be described in detail with reference to Examples of formation of pharmaceutical preparations of the carcinostatic composition of the present invention and Experiments illustrating the above $SV_{40}$ test and clinical treatments using these pharmaceutical preparations.

EXAMPLE 1

(liquid preparation for injection and infusion)

2000 mg of 4,6-O-benzylidene-D-glucopyranose was distributed in vials and sealed therein in a sterilized manner. An inert gas such as nitrogen or helium was introduced into the vials. The vials were stored in a cold and dark place. Just before administration, 500 ml of a 0.85% physiological saline solution was added to the stored active ingredient to form a liquid preparation for intravenous injection. The liquid preparation was administered by intravenous injection or intravenous infusion in an amount of 5 to 200 ml per day, which was appropriately adjusted depending on the condition of the disease.

EXAMPLE 2

(preparation for injection and capsules)

A solution of 60 mg of 4,6-O-benzylidene-D-glucopyranose in 1 g of refined sesame oil and 100 mg of an aluminum stearate gel was sealed in a vessel. An inert gas such as nitrogen or helium was introduced into the vessel. The vessel was stored in a cold and dark place. The preparation was used as a liquid preparation for subcutaneous injection. The preparation was administered in an amount of 0.2 to 10 ml per day, adjusted depending on the condition of the disease, by subcutaneous injection.

The above liquid preparation was distributed in capsules so that each capsule contained 0.5 ml of the preparation. The encapsulated preparation was orally administered at a dosage of 1 to 20 capsules per day, which was appropriately adjusted according to the condition of the disease.

EXAMPLE 3

(enteric tablets)

1000 enteric tablets (a) for adults and 1000 enteric tablets (b) for children were prepared from the following compositions (A) and (B):

|  | (a) | (b) |
|---|---|---|
| Composition (A): |  |  |
| Main ingredient (4,6-0-benzylidene-D-glucopyranose) | 100 g | 50 g |
| Lactose | 99.4 g | 49.7 g |
| Hydroxypropyl cellulose | 0.6 g | 0.3 g |
| Magnesium stearate | 2.0 g | 1.0 g |
| Composition (B): |  |  |
| Cellulose acetate phthalate | 6.0 g | 4.0 g |
| Hydroxypropylmethyl cellulose phthalate | 6.0 g | 4.0 g |
| Acetone-Ethanol (1:1) | 120 ml | 80 ml |

The ingredients of the composition (A) were sufficiently blended, and the mixture was either directly compressed to obtain tablets, or sufficiently kneaded and passed through a screen of an extrusion granulator to form granules which were then sufficiently dried and compressed to obtain tablets.

The tablets were then coated with the composition (B) in the form of a homogeneous solution to obtain enteric tablets.

These tablets were subjected to the disintegration test of the Pharmacopeia of Japan, that is, the disintegration test regarding enteric preparations using an artificial gastric juice (having a pH of 1.2). It was found that the tablets did not disintegrate even if shaken for 1 hour in the gastric juice, but that they disintegrated in 5 to 6 minutes in an artificial intestinal juice (having a pH of 7.5).

EXAMPLE 4

(enteric granules)

Enteric granules were prepared from the following compositions (A) and (B):

| Composition (A) | |
|---|---|
| Main ingredient (4,6-0-benzylidene-D-glucopyranese) | 100 g |
| Lactose | 737 g |
| hydroxypropyl cellulose | 3 g |
| Composition (B) | |
| Cellulose acetate phthalate | 80 g |
| Hydroxypropylmethyl cellulose phthalate | 80 g |
| Acetone Ethanol (1:1) | 1600 ml |

The ingredients of the composition (A) were sufficiently blended, and the mixture was formed into granules according to customary procedures. The granules were sufficiently dried and passed through a sieve to obtain granules suitable for bottle packing or heat seal packaging. While the granules were being suspended and fluidized, they were coated with the composition (B) in the form of a solution to obtain enteric granules. When the granules were subjected to a disintegration test using the disintegration tester of the Pharmacopoeia of Japan, it was found that they did not disintegrate while subjected to shaking for one hour in an artificial gastric juice having a pH of 1.2, but that they disintegrated in 5 minutes in an artificial intestinal juice having a pH of 7.5.

EXAMPLE 5

(enteric capsules)

1000 enteric capsules were prepared from the following compositions (A) and (B):

| | (a) | (b) |
|---|---|---|
| Composition (A): | | |
| Main ingredient (4,6-0-benzylidene-D-glucopyranose) | 100 g | 50 g |
| Lactose | 24.6 g | 74.4 g |
| Hydroxyproyl cellulose | 0.4 g | 0.4 g |
| Composition (B): | | |
| Cellulose acetate phthalate | 10 g | 10 g |
| Hydroxypropylmethyl cellulose phthalata | 10 g | 10 g |
| Acetone-Ethanol (1:1) | 200 ml | 200 ml |

In the same manner as described in Example 4, enteric granules suitable for capsules were prepared from the above compositions (A) and (B), and the granules were encapsulated to obtain enteric capsules.

When the capsules were subjected to a disintegration test using the disintegration tester of the Pharmacopoeia of Japan, it was found that they did not disintegrate or dissolve out even if they were shaken for one hour in an artificial gastric juice having a pH of 1.2, but that they completely disintegrate or dissolved out in 5 minutes in an artificial intestical juice having a pH of 7.5.

EXPERIMENT 1

($SV_{40}$ test)

The proliferation inhibition ratio (%) of 4,6-O-benzylidene-D-glucopyranose was determined according to the above-mentioned $SV_{40}$ method using W2K.11 cells obtained by malignant transformation of normal kidney cells of C3H mice by oncogenic virus $SV_{40}$. It was found that the proliferation inhibition ratio was 72% at a concentration of 500 mcg/ml with 72 hours of treatment, and that the proliferation inhibition ratios were 37% and 23%, respectively when the concentrations were 250 mcg/ml and 125 mcg/ml.

These results proved that the active ingredient of the present invention, that is, 4,6-O-benzylidene-D-glucopyranose, has an excellent carcinostatic activity in a broad concentration range.

Most conventional carcinostatic chemotherapeutic agents have a low carcinostatic activity toward malignant cells induced by oncogenic virus $SV_{40}$ than tumor cells transplanted in animals. Accordingly, it must be noted that the active ingredient of the present invention is distinguished from the conventional carcinostatic agents in that the active ingredient of the present invention acts on such induced malignant cells (primary carcinomata) and exerts a marked inhibiting effect.

More specifically, most conventional carcinostatic agents of the cytotoxic type have a prominent effect upon experimental tumors, that is, transplanted tumors, but they involve various unsolved problems in connection with actual clinical treatments and few of them exert effects as good as the clinical effects of the active ingredient of the present invention, described in the following Experiments. It is considered that this may be due to the fundamental difference between the transplanted tumor and the primary induced tumor. It is apparent that the active ingredient of the present invention, which exhibits activity toward a malignant cells induced by $SV_{40}$ virus that may be regarded as an artificially induced primary tumor, has a very characteristic carcinostatic activity.

EXPERIMENT 2

(colon carcinoma)

Patient:

Male, 36 years old, colon carcinoma with metastatic cancer of 13 cm × 10 cm × 8 cm in the liver, abdominal dropsy observed.

The patient was subjected to abdominal surgery on June 4, 1979 but extraction of the cancer was impossible and the incised abdoment was immediately sutured. Radiotherapy with cobalt 60 ($^{60}Co$) and FT 207 treatment, initiated before the operation, had been continued, but no effect had been observed.

Administration of 4,6-O-benzylidene-D-glucopyranose at a dosage of 20 mg/day/man (in the form of a physiological saline solution having an active ingredient concentration of 4 mg/ml) by intraperitoneal injection was stated on Aug. 25, 1979. The preparation for injection was prepared according to Example 1. In about one month, the abdominal dropsy disappeared, appetite improved and the overall body condition improved. From the C.T. scan (X-ray tomogram), it was found that contraction of the metastatic lesion in the liver had started. When the administration was continued for about 3 months, the metastatic lesion almost disappeared, and the CEA unit value (the hepatic function test) was remarkably reduced. In about 4 months, the metastatic lesion in the liver completely disappeared. The patient has lead a normal life since then.

Figure 1B:
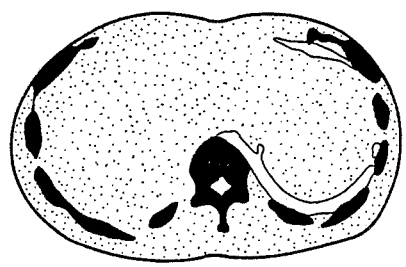

A C.T. scan of the liver of the patient before the start of the intraperitoneal injection, that was taken on Aug. 25, 1979, is shown in FIG. 1-A (the metastic lesion (A) appears on the left-side of the tomogram), and a C.T. scan of the same region taken on Dec. 29, 1979, that is, after passage of about 4 months from the start of the administration, is shown in FIG. 1-B. When FIG. 1-A is compared with FIG. 1-B, it will readily be understood that the metastatic lesion in the liver completely disappeared.

EXPERIMENT 3

(tongue cancer)

Patient:

Male, 28 years old, tongue cancer of the terminal stage, metastatis to the trachea and lung.

The patient had been subjected to the conventional chemotherapy, BCG treatment, radiotherapy and laetrile (amygdalin) treatment, but no effect could be observed. Spread of the cancer continued. The body weight of the patient was about ½ of normal body weight.

Administration of 4,6-O-benzylidene-D-glucopyranose at a dosage of 200 mg/day/man by intravenous infusion was started on Oct. 15, 1979. The preparation for infusion was prepared according to Example 1. After 10 days of treatment, the tumor on the tongue began to disappear and the submaxillar tumor softened and began to release a granular substance. It was also found that the granular substance released from the submaxillar was composed of histopathologically keratinized squamous cells.

Figure 2A:
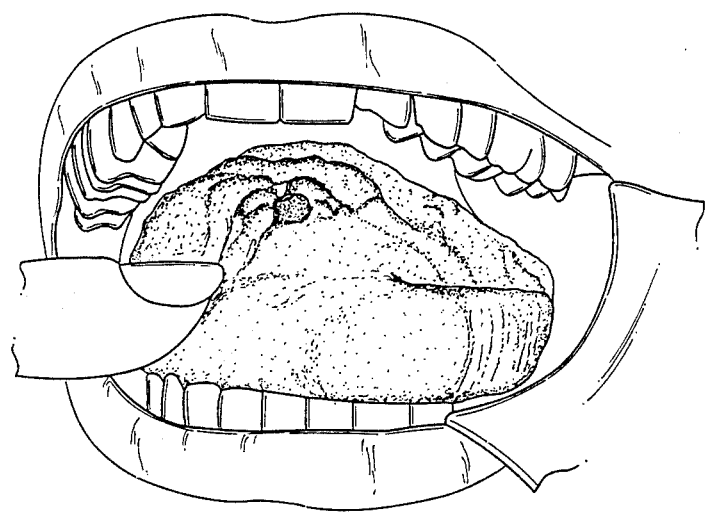
FIG. 2-A is a photograph showing the affected region of a patient suffering from the cancer of the tongue cancer before the treatment with the carcinostatic composition of the present invention.
Figure 2B:
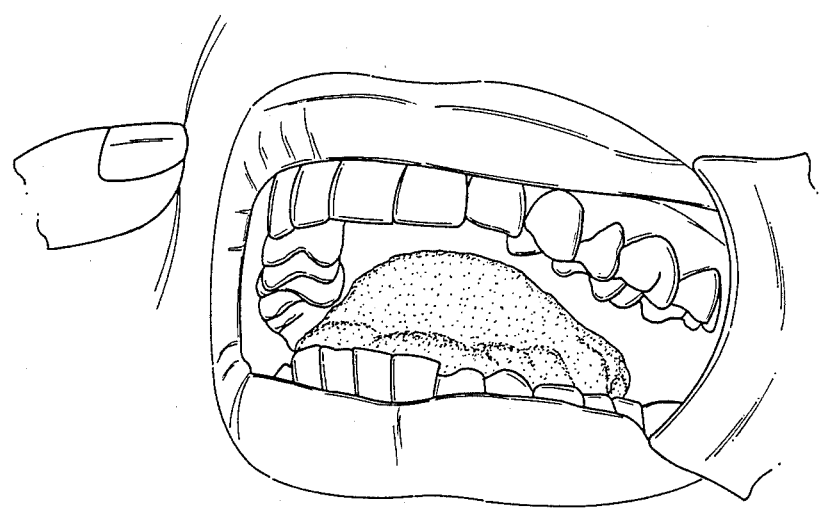

A photograph of the tongue of the patient taken before the start of the administration on Oct. 15, 1979 is shown in FIGS. 2-A and 3-A, and a photograph of the same region taken in the same direction on Nov. 19, 1979 is shown in FIGS. 2-B and 3-B. When FIGS. 2-A and 3-A are compared with FIGS. 2-B and 3-B, respectively, it will readily be understood that the malignant lesion disappeared.

However, since the condition of the patient's disease was already in the terminal stage and the patient had been extremely enfeebled, the patient died after about one month of treatment.

EXPERIMENT 4

(peritonitis cartinimatosa)

Patient:

Male, 37 years old, peritonitis cartinimatosa with metastatis throughout entire body, large quantity of abdominal dropsy observed.

Administration of 4,6-O-benzylidene-D-glucopyranose at a dosage of 200 mg/day/man by intravenous infusion was started for the treatment of the patient. The preparation for infusion was prepared according to Example 1. After one week's administration, the abdominal dropsy disappeared, and subjective and objective improvements in the condition of the disease were observed with contraction of the cancer metastasized to the skin. However, the patient died of paritonitis periforative about one month after the start of treatment.

EXPERIMENT 5

(primary liver tumor)

Patient:

Male, 58 years old, primary liver tumor of the terminal stage, large quantity of abdominal dropsy observed.

4,6-O-benzylidene-D-glucopyranose was continuously administered at a dosage of 200 mg/day/man by intravenous infusion. The preparation for infusion was prepared according to Example 1. A reduction in the abdominal dropsy and prominent contraction of the liver tumor were observed about one month after the start of treatment, but the patient died after about four months of treatment.

EXPERIMENT 6

(stomach cancer)

Patient:

Stomach cancer of the terminal stage, the stomach extracted but many metastasized lesion in abdominal cavity, peritonitis cartinimatosa observed.

4,6-O-benzylidene-D-glucopyranose was continuously administered to the patient at a dosage of 200 mg/day/man by intravenous infusion. The preparation for infusion was prepared according to Example 1. After one month of administration, the abdominal dropsy disappeared and the subjective symptoms showed remarkable improvement. However, the patient died about 3 months after the start of administration.

What we claim is:

1. A composition, effective against a malignant condition which is carcinoma of the colon, cancer of the stomach, cancer of the tongue, peritonitis carcinomatosa, cancer of the liver or malignancies induced by $SV_{40}$ virus, which comprises 4,6-O-benzylidene-D-glucopyranose as the active ingredient in the form of a sterile injection preparation or a sterile intravenous drip preparation in unit dosage form containing a dosage of about 0.5 to about 5000 mg of 4,6-O-Benzylidene-D-glucopyranose in the liquid concentration, wherein the injection preparation is in the form of a solution, emulsion, suspension or oil base and the intravenous drip preparation is in the form of a sterile solution, emulsion or suspension, and at least one inert carrier.

2. A preparation according to claim 1, which comprises 4,6-O-benzylidene-D-glucopyranose as the active ingredient in the form of a sterile intraperitoneal injection preparation or a sterile intravenous drip preparation containing a dosage of about 20 to about 200 mg of 4,6-O-benzylidene-D-glucopyranose.

3. A composition, effective against a malignant condition which is carcinoma of the colon, cancer of the stomach, cancer of the tongue, peritonitis carcinomatosa, cancer of the liver or malignancies induced by $SV_{40}$ virus, which comprises 4,6-O-benzylidene-D-glucopyranose as the active ingredient in the form of an enteric tablet or enteric granule or a capsule containing a dosage of about 1.5 to about 15000 mg of 4,6-O-benzylidene-D-glucopyranose and at least one inert carrier.

4. The composition according to claim 3, wherein the inert carrier is a member selected from the group consisting of surface active agents, excipients, lubricants, adjuvants, pharmaceutically acceptable film forming agents and coating assistants.

5. A method of causing at least temporary relief to humans and animals suffering from a malignant condition which is carcinoma of the colon, cancer of the stomach, cancer of the tongue, peritonitis carcinomatosa, cancer of the liver or malignancies induced by $SV_{40}$ virus, which consists of administering to said humans and animals an amount effective to cause regression of the carcinoma of a composition comprising 4,6-O-benzylidene-D-glucopyranose as the active ingredient in the form of an injection preparation or an intravenous drip preparation containing a dosage of about 0.5 to about 5000 mg per day of 4,6-O-benzylidene-D-glucopyranose.

6. The method according to claim 5, wherein the dosage is about 20 to about 200 mg per day of 4,6-O-benzylidene-D-glucopyranose.

7. A method of causing at least temporary relief to humans and animals suffering from a malignant condition which is carcinoma of the colon, cancer of the stomach, cancer of the tongue, peritonitis carcinomatosa, cancer of the liver or malignancies induced by $SV_{40}$ virus, which consists of administering to said humans and animals an amount effective to cause regression of the carcinoma of a composition comprising 4,6-O-benzylidene-D-glucopyranose as the active ingredient in the form of an enteric tablet or enteric granule or a capsule containing a dosage of about 1.5 to about 15000 mg per day of 4,6-O-benzylidene-D-glucopyranose.

* * * * *

UNITED STATES PATENT AND TRADEMARK OFFICE
CERTIFICATE OF CORRECTION

PATENT NO. : 4,882,314

DATED : November 21, 1989

INVENTOR(S) : Setsuo Takeuchi, Mutsuyuki Kochi, Akira Kawarada, Shinichiro Esumi, Kazuya Sasaki, Shozo Kawabata, It is certified that error appears in the above-identified patent and that said Letters Patent is hereby corrected as shown below:

On the title page, item [75],

Kaguya Sasaki is incorrectly spelled and should read Kazuya Sasaki.

Signed and Sealed this

Fourth Day of June, 1991

Attest:

HARRY F. MANBECK, JR.

Attesting Officer

Commissioner of Patents and Trademarks